United States Patent
Barak et al.

(10) Patent No.: US 10,254,218 B2
(45) Date of Patent: Apr. 9, 2019

(54) METHOD FOR QUANTIFYING THE AMOUNT OF AMMONIUM BICARBONATE IN A SOLID SAMPLE OF AMMONIUM BICARBONATE

(71) Applicant: A.Y. Laboratories Ltd., Tel Aviv (IL)

(72) Inventors: Ayala Barak, Tel Aviv (IL); Mari Nuopponen, Krefeld (DE)

(73) Assignee: A.Y. LABORATORIES LTD., Tel Aviv (IL)

( * ) Notice: Subject to any disclaimer, the term of this patent is extended or adjusted under 35 U.S.C. 154(b) by 0 days.

(21) Appl. No.: 15/314,552

(22) PCT Filed: Jun. 2, 2015

(86) PCT No.: PCT/IL2015/050568
§ 371 (c)(1),
(2) Date: Nov. 29, 2016

(87) PCT Pub. No.: WO2015/193876
PCT Pub. Date: Dec. 23, 2015

(65) Prior Publication Data
US 2017/0199121 A1 Jul. 13, 2017

Related U.S. Application Data

(60) Provisional application No. 62/013,154, filed on Jun. 17, 2014.

(51) Int. Cl.
*G01J 5/02* (2006.01)
*G01N 21/3563* (2014.01)
(Continued)

(52) U.S. Cl.
CPC ......... *G01N 21/3563* (2013.01); *C01B 21/12* (2013.01); *G01N 21/278* (2013.01);
(Continued)

(58) Field of Classification Search
CPC .......... G01J 3/02; G01J 3/0216; G01J 3/0218; G01J 3/10; G02B 6/4298; G02B 6/4206;
(Continued)

(56) References Cited

U.S. PATENT DOCUMENTS

| 6,865,408 B1 | 3/2005 | Abbink et al. |
| 8,431,886 B2 | 4/2013 | Grothe |

(Continued)

FOREIGN PATENT DOCUMENTS

| CN | 101051024 A | 10/2007 |
| JP | H10-19771 | 1/1998 |

(Continued)

OTHER PUBLICATIONS

Meng, Lingyu, et al. "Development of an analytical method for distinguishing ammonium bicarbonate from the products of an aqueous ammonia CO2 scrubber." Analytical chemistry 77.18 (2005): 5947-5952.

(Continued)

*Primary Examiner* — Kiho Kim

(57) ABSTRACT

A method for quantifying the amount of ammonium bicarbonate in a solid sample of ammonium carbamate is provided. The method includes measuring the FT-IR spectrum of the sample, calculating the IR band maximum for a first band that is common to ammonium carbamate and ammonium bicarbonate and for a second band that is unique to ammonium carbamate, calculating a ratio of the maximum of the second band to the maximum of the first band, and calculating the concentration of ammonium bicarbonate in the sample from a calibration curve.

11 Claims, 2 Drawing Sheets

(51) Int. Cl.
  *G01N 21/49* (2006.01)
  *G01N 21/27* (2006.01)
  *C01B 21/12* (2006.01)
  *G01N 21/552* (2014.01)
  *G01N 21/35* (2014.01)

(52) U.S. Cl.
  CPC ........... *G01N 21/49* (2013.01); *G01N 21/552* (2013.01); *G01N 2021/3595* (2013.01)

(58) Field of Classification Search
  CPC .. G01N 21/278; G01N 21/4785; G01N 21/49; G01N 2201/1293; G01N 21/3563; G01N 21/552; G01N 2021/3595
  See application file for complete search history.

(56) References Cited

U.S. PATENT DOCUMENTS

| | | | | |
|---|---|---|---|---|
| 9,091,676 | B2* | 7/2015 | Rule | A61B 5/1427 |
| 9,869,585 | B2* | 1/2018 | Schiering | G01J 3/0256 |
| 2011/0112772 | A1 | 5/2011 | Yost et al. | |
| 2014/0199620 | A1* | 7/2014 | Ishida | G03G 5/0614 |
| | | | | 430/57.1 |
| 2014/0315318 | A1* | 10/2014 | Lu | G01N 33/15 |
| | | | | 436/93 |
| 2015/0192462 | A1* | 7/2015 | Schiering | G01J 3/44 |
| | | | | 250/208.2 |

FOREIGN PATENT DOCUMENTS

| | | |
|---|---|---|
| WO | 2014/009533 | 1/2014 |
| WO | 2015/193876 | 12/2015 |

OTHER PUBLICATIONS

Nasrazadani, Seifollah, and Esteban Eureste. Application of FTIR for quantitative lime analysis. Denton, TX, USA: University of North Texas, 2008.

Suart, B. "Infrared Spectroscopy: Fundamental and Applications." (2004): 138-141.

FTIR Spectroscopy Jan. 2013; [retrieved Sep. 23, 2015], Retrieved from the Internet: URL: http://chemistry.oregonstate.edu/courses/ch361-464/ch362/irinstrs.htm.

Park, HoSeok, et al. "Analysis of the CO2 and NH3 reaction in an aqueous solution by 2D IR COS: Formation of bicarbonate and carbamate." the Journal of Physical Chemistry A 112.29 (2008): 6558-6562.

Khanna, R. K., and M. H. Moore. "Carbamic acid: molecular structure and IR spectra." Spectrochimica Acta Part A: Molecular and Biomolecular Spectroscopy 55.5 (1999): 961-967.

An International Search Report 2015, and a Written Opinion both dated Oct. 30, 2015, which issued during the prosecution of Applicant's PCT/IL2015/050568.

An International Preliminary Report on Patentability dated Dec. 20, 2016, which issued during the prosecution of Applicant's PCT/IL2015/050568.

U.S. Appl. No. 62/013,154, filed Jun. 17, 2014.

An Office Action together with the English translation dated Dec. 25, 2018, which issued during the prosecution of Japanese Patent Application No. 2016-571292.

* cited by examiner

METHOD FOR QUANTIFYING THE AMOUNT OF AMMONIUM BICARBONATE IN A SOLID SAMPLE OF AMMONIUM BICARBONATE

RELATED APPLICATIONS

This application is a National Phase Application of PCT International Application No. PCT/IL2015/050568, International Filing Date Jun. 2, 2015, which claims priority to U.S. Provisional Patent Application Ser. No. 62/013,154, filed Jun. 17, 2014.

CROSS-REFERENCE TO RELATED APPLICATION

Reference is made to U.S. Provisional Patent Application Ser. No. 62/013,154, filed Jun. 17, 2014 and entitled METHOD FOR QUANTIFYING THE AMOUNT OF AMMONIUM BICARBONATE IN A SOLID SAMPLE OF AMMONIUM CARBAMATE, the disclosure of which is hereby incorporated by reference and priority of which is hereby claimed pursuant to 37 CFR 1.78(a)(4) and (5)(i).

FIELD OF THE INVENTION

The present invention relates to a method for quantifying the amount of ammonium bicarbonate in a solid sample of ammonium carbamate.

BACKGROUND OF THE INVENTION

Various techniques are known for quantifying ammonium carbonate, ammonium bicarbonate and ammonium carbamate in a sample.

SUMMARY OF THE INVENTION

The present invention seeks to provide a method for quantifying the amount of ammonium bicarbonate in a solid sample of ammonium carbamate.

There is thus provided in accordance with a preferred embodiment of the present invention a method for quantifying the amount of ammonium bicarbonate in a solid sample of ammonium carbamate including:
 a. measuring the FT-IR spectrum of the sample;
 b. calculating the IR band maximum for a first band that is common to ammonium carbamate and ammonium bicarbonate and for a second band that is unique to ammonium carbamate;
 c. calculating a ratio of the maximum of the second band to the maximum of the first band; and
 d. calculating the concentration of ammonium bicarbonate in the sample from a calibration curve relating the concentration to the ratio.

In a preferred embodiment of the present invention, the measuring the FT-IR spectrum of the sample includes measuring the attenuated total reflectance of the solid sample when pressed against a crystal. Preferably, the crystal is a diamond crystal.

In a preferred embodiment of the present invention, the first band is 2781-2875 cm$^{-1}$. In another preferred embodiment of the present invention, the second band is 3423-3500 cm$^{-1}$. In a preferred embodiment of the present invention, the maximum for a first band and the maximum for a second band are each corrected by subtracting the average absorbance in a background band. Preferably, the background band is 3870-3999 cm$^{-1}$.

In a preferred embodiment of the present invention, the calibration curve is constructed by:
 a. preparing a plurality of calibration samples including known quantities of ammonium carbamate and ammonium bicarbonate;
 b. measuring the FT-IR spectrum of each of the plurality of calibration samples;
 c. for each of the plurality of calibration samples, calculating the IR band maximum for the first band and for the second band;
 d. for each of the plurality of calibration samples, calculating a ratio of the maximum of the second band to the maximum of the first band; and
 e. creating a regression curve of the bicarbonate composition as a function of the ratio.

Preferably, the regression curve is a second-order polynomial curve. In a preferred embodiment of the present invention, the regression coefficient of the regression curve is at least 0.99. Preferably, the calibration curve is reconstructed once a month.

BRIEF DESCRIPTION OF THE DRAWING

The present invention will be understood and appreciated more fully from the following detailed description, taken in conjunction with the drawing in which.

DETAILED DESCRIPTION OF THE INVENTION

Figure 1:
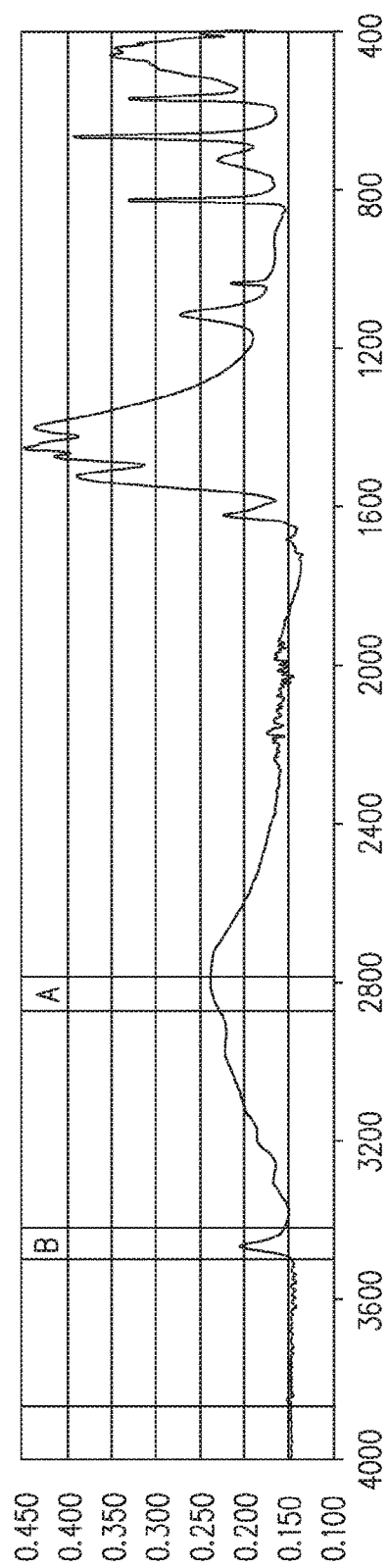
FIG. 1 is the FT-IR absorbance spectrum of ammonium carbamate.

Ammonium carbamate can be formed from the reaction of ammonia with carbon dioxide according to the following reaction:

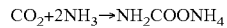

$$CO_2 + 2NH_3 \rightarrow NH_2COONH_4$$

Ammonium carbamate is an important intermediate in the production of urea, which is used as a nitrogen-releasing fertilizer, among other uses. The production of urea occurs according to the following reaction:

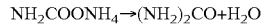

$$NH_2COONH_4 \rightarrow (NH_2)_2CO + H_2O$$

The major impurity in ammonium carbamate is ammonium bicarbonate, which is formed by the reaction of ammonium carbamate with water according to the following reaction:

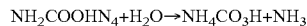

$$NH_2COOHN_4 + H_2O \rightarrow NH_4CO_3H + NH_3$$

Accordingly, it is important to be able to determine the purity of ammonium carbamate, and in particular to quantify the amount of ammonium bicarbonate in ammonium carbamate.

Various methods are known for identifying and quantifying ammonium carbamate, ammonium carbonate and ammonium bicarbonate in a sample. Burrows et al., J. Am. Chem. Soc. (1912), 34(8):993-995 discloses a method of separating ammonium carbamate from ammonium carbonate by selective precipitation of carbonate with barium salts. The separated fractions are titrated with hydrochloric acid. Lugowska, Zeszyty Naukowe Politechniki Slaskiej, Chemia (1972), 60:29-37 discloses a method of separation carbamate from carbonate and bicarbonate by dissolution of the sample in acetone. Carbamate is soluble in acetone while carbonate and bicarbonate are insoluble. After separation, both fractions are titrated with perchloric acid.

Byun, Kongop Hwahak (1994), 5(4):657-661 discloses a method of quantifying ammonium carbamate and urea in a sample using IR spectroscopy. Absorption peaks in the near IR (NIR) range were used to distinguish between ammonium carbamate and urea. In this method, ammonia is used to inhibit the decomposition of ammonium carbamate to ammonium bicarbonate.

Meng et al., Anal. Chem. (2005), 77(18): 5947-5952 discloses a method for measuring the purity of a sample containing mainly ammonium bicarbonate using a combination of NIR spectroscopy and elemental analysis. It is also disclosed that ammonium carbamate can be qualitatively identified using FT-IR (Fourier transform infrared) spectroscopy.

Mani et al., Green Chem. (2006), 8:995-1000 discloses a method of determining the relative concentrations of carbamate, carbonate and bicarbonate using $^{13}C$ NMR. There do not appear to be any known methods for quantifying ammonium bicarbonate in a solid sample of ammonium carbamate using FT-IR spectroscopy.

In accordance with a first embodiment of the present invention, there is provided a method for quantifying the amount of ammonium bicarbonate in a solid sample of ammonium carbamate comprising:
 a. measuring the FT-IR spectrum of the sample;
 b. calculating the IR band maximum for a first band that is common to ammonium carbamate and ammonium bicarbonate and for a second band that is unique to ammonium carbamate;
 c. calculating a ratio of the maximum of the second band to the maximum of the first band; and
 d. calculating the concentration of ammonium bicarbonate in the sample from a calibration curve relating said concentration to said ratio.

In one embodiment, the FT-IR spectrum is measured using a Nicolet® 6700 FT-IR spectrometer (Thermo Fisher Scientific, Waltham, Mass. USA). FT-IR spectra are preferably collected directly from solid, homogenized samples without any additional sample preparation using the ATR (Attenuated Total Reflectance) technique. The samples are preferably pressed against a diamond ATR crystal.

Preferably, the spectral data are recorded in the mid infrared range (4000-400 $cm^{-1}$). The sampling depth is typically in the range of 0.3-3 µm. A background spectrum is preferably recorded against a clean diamond ATR crystal prior to each sample measurement.

Figure 2:
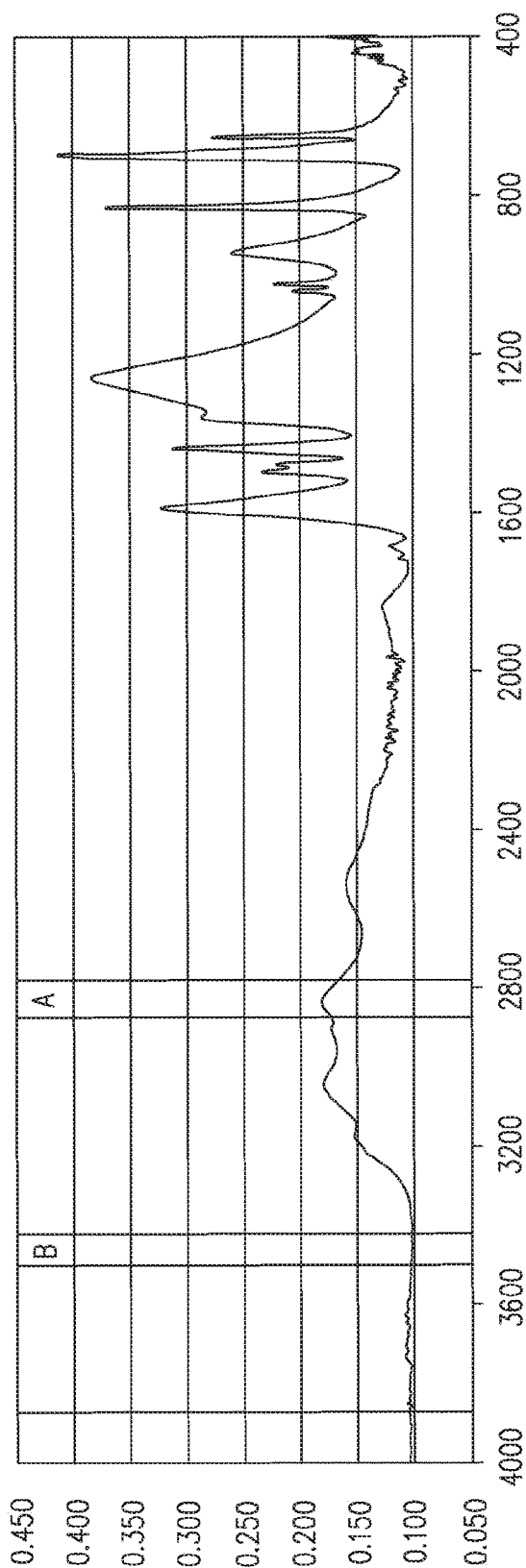
FIG. 2 is the FT-IR absorbance spectrum of ammonium bicarbonate.

FIG. 1 shows the FT-IR spectrum of high-purity ammonium carbamate (BASF, Ludwigshafen, Germany). FIG. 2 shows the FT-IR spectrum of reagent grade ammonium bicarbonate. It can be seen from these two spectra that ammonium carbamate has an absorption band centered at 3465 $cm^{-1}$, while ammonium bicarbonate has no absorption band at that wavenumber.

In one embodiment, the first hand common to ammonium carbamate and ammonium bicarbonate is 2781-2875 $cm^{-1}$. The maximum absorbance in this band is preferably corrected for background noise by subtracting the average absorbance in the band 3870-3999 $cm^{-1}$. The resulting value is called value A.

In one embodiment, the second band unique to ammonium carbamate that is not present in the FT-IR spectrum of ammonium bicarbonate is 3423-3500 $cm^{-1}$. The maximum absorbance in this band is preferably corrected for background noise by subtracting the average absorbance in the band 3870-3999 $cm^{-1}$. The resulting value is called value B. These bands are shown in FIGS. 1 and 2. The ratio B/A is called value C.

The calibration curve is preferably constructed by:
 e. preparing a plurality of calibration samples comprising known quantities of ammonium carbamate and ammonium bicarbonate;
 f. measuring the FT-IR spectrum of each of the calibration samples;
 g. calculating the value C for each of the calibration samples; and
 h. creating a regression curve of the bicarbonate composition as a function of the value C.

In one embodiment, the calibration samples are prepared from high purity ammonium carbamate and reagent grade ammonium bicarbonate. The calibration samples also preferably include samples of pure ammonium carbamate, pure ammonium bicarbonate and pure commercial ammonium carbonate. Commercial ammonium carbonate is a 1:1 molar ratio of ammonium carbamate and ammonium bicarbonate. Since it is expected that the levels of bicarbonate impurities in ammonium carbamate will be low, the calibration samples preferably include several samples at the low end of the bicarbonate concentration range, such as 1%, 5%, 10%, 15% and 20%.

The regression curve can be any curve that fits the calibration data. In a preferred embodiment, the calibration curve is a second-order polynomial curve. Preferably the regression coefficient R is at least 0.99. Preferably, the FT-IR instrument is recalibrated once a month. Since bicarbonate is the major impurity in the sample, the sample purity can be estimated as 100%—bicarbonate concentration (%).

EXAMPLES

Example 1

Calibration samples were prepared by mixing different amounts of ammonium bicarbonate (>99%, BDH, Radnor, Pa., USA) with high purity ammonium carbamate (BASF, Ludwigshafen, Germany) as detailed in Table 1. In addition, a sample of pure commercial ammonium carbonate (Merck, Darmastadt, Germany), which is a 1:1 molar ratio of ammonium bicarbonate and ammonium carbamate, was taken for the calibration. Two samples for each concentration were used. All calibration samples were homogenized with an MM 400 ball mill (Retsch, Haan, Germany) for 1 minute at 30 Hz prior to FT-IR analysis.

TABLE 1

FT-IR calibration samples.

| Amount of ammonium carbamate, w/w (%) | Amount of ammonium bicarbonate, w/w (%) |
|---|---|
| 100 | 0 |
| 99 | 1 |
| 95 | 5 |
| 90 | 10 |
| 85 | 15 |
| 80 | 20 |
| 0 | 100 |

FT-IR spectra were collected directly from the homogenized samples without any additional sample preparation using the ATR technique. A diamond ATR crystal was utilized. The spectral data were recorded in the mid infrared range (4000-400 cm$^{-1}$) using a resolution of 4 cm$^{-1}$ and 120 scans. A background spectrum was recorded against a clean diamond ATR crystal prior to each sample measurement.

For each spectrum the IR band maximum between 2781-2875 cm$^{-1}$ was taken and the average of the background signals in the spectral region of 3870-3999 cm$^{-1}$ was subtracted therefrom to provide value A. In addition, the IR band maximum between 3423-3500 cm$^{-1}$ was taken and the average of the background signals in the spectral region of 3870-3999 cm$^{-1}$ was subtracted therefrom to provide value B. The value B/A is the value C.

The ammonium bicarbonate concentration was plotted as a function of the C value. The data were fit to regression curves. Polynomial regression gave the best fit, with a regression constant of 0.9932 and a formula $$y = 1.774 C^2 - 2.6565 C + 0.9963$$

wherein y is the ammonium bicarbonate concentration (w/w).

The FT-IR spectra of two samples from each of two industrial batches of ammonium carbamate were measured and the C values calculated as for the calibration samples. The bicarbonate concentrations calculated from the calibration curve and the sample purities are reported in Table 2.

TABLE 2

Ammonium bicarbonate concentration industrial samples of carbamate

| Batch | C value | Bicarbonate concentration (%) | Sample purity (%) |
|---|---|---|---|
| 1 | 0.528281 | 8 | 92 |
| 1 | 0.544591 | 7 | 93 |
| 2 | 0.585135 | 5 | 95 |
| 2 | 0.582629 | 5 | 95 |

Example 2

A calibration curve was prepared as described in Example 1. Polynomial regression gave the best fit, with a regression constant of 0.9944 and a formula $$y = 16588 C^2 - 2.6148 C + 1.0215$$

wherein y is the ammonium bicarbonate concentration (w/w).

The FT-IR spectra of industrial batches of ammonium carbamate from three different producers were measured and the C values calculated as for the calibration samples. The bicarbonate concentrations calculated from the calibration curve and the sample purities are reported in Table 3.

TABLE 3

Ammonium bicarbonate concentration in industrial samples of carbamate

| Batch | C value | Bicarbonate concentration (%) | Sample purity (%) |
|---|---|---|---|
| D1 | 0.677193 | 1 | 99 |
| D1 | 0.648803 | 2 | 98 |
| D2 | 0.596883 | 5 | 95 |
| D2 | 0.58691 | 6 | 94 |
| D3 | 0.595691 | 5 | 95 |
| D3 | 0.610847 | 4 | 96 |
| D4 | 0.603204 | 5 | 95 |
| D4 | 0.640028 | 3 | 97 |
| D5 | 0.558668 | 8 | 92 |
| D5 | 0.51993 | 11 | 89 |
| S1 | 0.507155 | 12 | 88 |
| S1 | 0.493468 | 14 | 86 |
| S2 | 0.590611 | 6 | 94 |
| S2 | 0.616511 | 4 | 96 |
| S3 | 0.629779 | 3 | 97 |
| S3 | 0.640886 | 3 | 97 |
| S4 | 0.449107 | 18 | 82 |
| S4 | 0.468347 | 16 | 84 |
| S5 | 0.506865 | 12 | 88 |
| S5 | 0.506601 | 12 | 88 |
| B1 | 0.639531 | 3 | 97 |
| B1 | 0.670934 | 1 | 99 |
| B2 | 0.671199 | 1 | 99 |
| B2 | 0.641169 | 3 | 97 |
| B3 | 0.621668 | 4 | 96 |
| B3 | 0.635751 | 3 | 97 |
| B4 | 0.595292 | 5 | 95 |
| B4 | 0.641512 | 3 | 97 |
| B5 | 0.63316 | 3 | 97 |
| B5 | 0.673346 | 1 | 99 |

It will be appreciated by persons skilled in the art that the present invention is not limited to what has been particularly shown and described hereinabove. Rather the scope of the present invention includes both combinations and subcombinations of various features described hereinabove as well as modifications thereof which would occur to a person of skill in the art upon reading the foregoing description and which are not in the prior art.

The invention claimed is:

1. A method for producing urea from a solid sample of ammonium carbamate comprising:
   a) measuring an FT-IR spectrum of said sample;
   b) calculating an IR band maximum for a first band that is common to ammonium carbamate and ammonium bicarbonate and for a second band that is unique to ammonium carbamate;
   c) calculating a ratio of said maximum of said second band to said maximum of said first band;
   d) calculating the concentration of ammonium bicarbonate in said sample from a calibration curve relating said concentration to said ratio; and
   e) reacting said sample to form urea.

2. The method according to claim 1, wherein said measuring the FT-IR spectrum of said sample comprises measuring an attenuated total reflectance of the solid sample when pressed against a crystal.

3. The method according to claim 2, wherein said crystal is a diamond crystal.

4. The method according to claim 1, wherein said first band is 2781-2875 cm$^{-1}$.

5. The method according to claim 1, wherein said second band is 3423-3500 cm$^{-1}$.

6. The method according to claim 1, wherein said maximum for a first band and said maximum for a second band are each corrected by subtracting an average absorbance in a background band.

7. The method according to claim 6, wherein said background band is 3870-3999 cm$^{-1}$.

8. The method according to claim 1, wherein said calibration curve is constructed by:

a) preparing a plurality of calibration samples comprising known quantities of ammonium carbamate and ammonium bicarbonate;
b) measuring an FT-IR spectrum of each of said plurality of calibration samples;
c) for each of said plurality of calibration samples, calculating an IR band maximum for said first band and for said second band;
d) for each of said plurality of calibration samples, calculating a ratio of said maximum of said second band to said maximum of said first band; and
e) creating a regression curve of bicarbonate composition as a function of said ratio.

9. The method according to claim 8, wherein said regression curve is a second-order polynomial curve.

10. The method according to claim 8, wherein a regression coefficient of said regression curve is at least 0.99.

11. The method according to claim 8, wherein said calibration curve is reconstructed once a month.

* * * * *